United States Patent [19]

Rosenthal

[11] Patent Number: 4,761,552
[45] Date of Patent: Aug. 2, 1988

[54] STANDARD FOR NEAR-INFRARED REFLECTANCE MEASUREMENT AND METHOD OF MAKING THE SAME

[75] Inventor: Robert D. Rosenthal, Gaithersburg, Md.

[73] Assignee: Trebor Industries, Inc., Gaithersburg, Md.

[21] Appl. No.: 907,890

[22] Filed: Sep. 16, 1986

[51] Int. Cl.⁴ .............................................. G01N 21/01
[52] U.S. Cl. .................................. 250/252.1; 356/243
[58] Field of Search ....................... 250/252.1; 356/243

[56] References Cited

U.S. PATENT DOCUMENTS 3,764,364 10/1973 Seiner .
3,956,201 5/1976 Seiner .
4,047,032 9/1977 Judge et al. .
4,095,105 6/1978 Rosenthal .......................... 250/252.1
4,647,198 3/1987 Sommer ........................... 250/252.1

OTHER PUBLICATIONS

Weidner, V. R. and J. J. Hsia, "Reflection Properties of Pressed Polytetrafluoroethylene Powder," *J. Opt. Soc. Am.*/vol. 71, No. 7/Jul. 1987.

*Primary Examiner*—Carolyn E. Fields
*Attorney, Agent, or Firm*—Bernard, Rothwell & Brown

[57] ABSTRACT

A fixed stable standard for near-infrared reflectance measurement is provided by using a sample holder having an IR-quartz window and a measured amount of PTFE powder pressed directly thereagainst so that the PTFE powder has a fixed density providing a permanent reflectance standard protected by the window, and a method of making the standard is also provided.

2 Claims, 1 Drawing Sheet

STANDARD FOR NEAR-INFRARED REFLECTANCE MEASUREMENT AND METHOD OF MAKING THE SAME

FIELD OF THE INVENTION

This invention relates to improvements in the art of standards for near-infrared reflecting measurements.

BACKGROUND AND PRIOR ART

Near-infrared reflectance type measuring instruments have found wide commercial acceptance for the measurement of organic properties for many foods and other types of materials. Reflectance type NIR instruments require a stable optical standard. To date, most of such instruments have used a standard of ceramic material such as disclosed in U.S. Pat. No. 4,047,032 to Judge et. al., assigned to Technicon Instruments Corp. The standard of this patent has a number of favorable features and advantages including good stability and high reflectivity. However, it does not have the optimum amount of reflectance nor is it consistent with other work performed at the National Bureau of Standards (NBS) to standardize such instruments. There is a need in the art for a standard for spectral reflectance which has an optimum amount of reflectance and is consistent with NBS leadership in the art.

U.S. Pat. Nos. 3,764,364 and 3,956,201, to Jerome A. Seiner and assigned to PPG Industries, Inc., disclose the use of pressed polytetrafluoroethylene (PTFE) powder for providing stable optical standards between 2,400 to 8,000 angstroms wave length range. These types of optical standards have been investigated by the National Bureau of Standards and the results published in the Journal of the Optical Society of America, Volume 71, pages 856-861, July 1981, titled "Reflection Properties of Pressed Polytetrafluoroethylene Powder" by Victor R. Weidner and Jack J. Hsia. The Seiner patents and this technical paper describe the use of PTFE powder as a standard material for reflectance measurements. However, the use of pressed PTFE powder has a significant limitation in that it is fragile and cannot handle normal conditions required in field use of instruments in which such standards would be used.

There is a need in the art to have a standard which can tolerate some of the normal handling conditions which occur in field use of instruments and still not degrade its optical characteristics.

SUMMARY OF THIS INVENTION

This invention provides a fixed stable standard for near-infrared reflectance measurement with an optimum reflectance wavelength range by utilizing a sample holder having a near-IR-quartz window and a measured amount of PTFE powder pressed directly against such IR-quartz window so as to have a fixed density and provide a permanent reflectance standard that is protected behind the quartz window. The invention also contemplates the method of making such standard by placing a measured amount of PTFE powder in the standard on top of an IR-quartz window and pressing this measured amount evenly and parallel to the surface of the IR-quartz window by a manually pressed piston to provide a permanent reflectance standard that is protected behind the quartz window.

DETAILED DESCRIPTION OF PREFERRED EMBODIMENT

Figure 3:
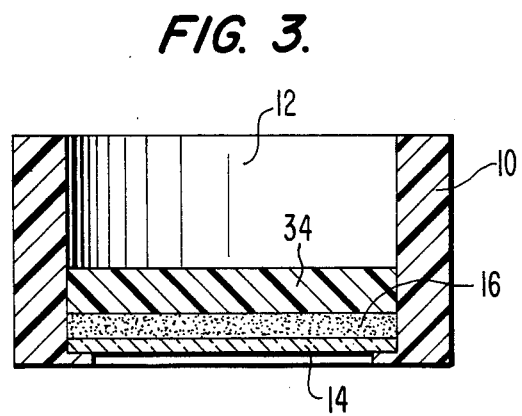
FIG. 3 is a sectional view of the standard after it has been manufactured.

A standard holder 10 has a cavity 12 therein. There is a near-IR-quartz window 14 in the bottom of the sample holder 10 as viewed in the drawings. The near-IR-quartz window avoids normal absorptions that occur in glass in the spectrum range between 1.0 and 2.5 micrometers. A pressed PTFE standard 16 is formed directly on the near-IR-quartz window as shown in FIG. 3. The material may be the same material mentioned in footnote 1 of the article cited above. The standard holder 10 has bottom lips 20 adjacent the near-IR-quartz window 14 and a smooth flat top surface 22. The distance H between the plane of the top surface 22 and the top of the window 14 is a precision distance as it determines the degree of pressing of the powdered PTFE.

A pressing piston 24 is provided for making the pressed PTFE standard disk on the near-IR-quartz window. It has a piston head 26 with parallel sidewalls 28 of a diameter equal to the internal diameter of the sample holder 10. The piston has a flat surface head 30 which is parallel to the flat undersurface 32 of flange 34. The distance between surface 32 and surface 30, together with the distance between surface 22 and surface 20 determines how far forward the piston travels into the standard holder and, depending upon the amount of PTFE powder in the standard holder, how densely the powder is pressed.

Figure 1:
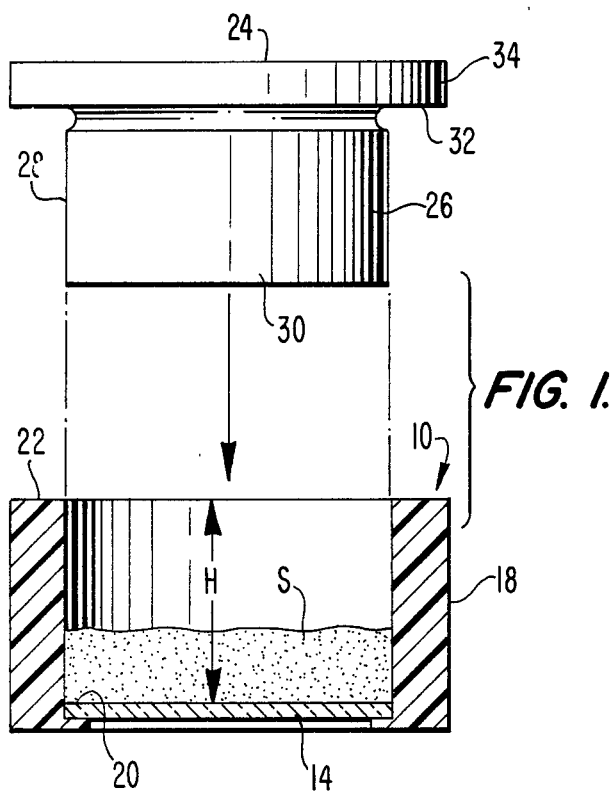
FIG. 1 is an exploded perspective view of the standard holder with powdered PTFE therein and a pressing piston.
Figure 2:
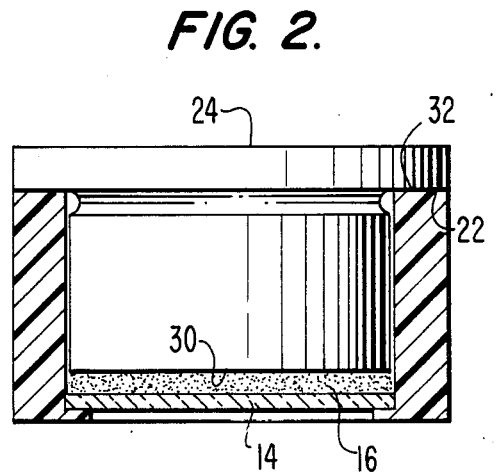
FIG. 2 shows the pressing piston in place, making the standard.

FIG. 2 shows making the standard in which the PTFE powder is pressed into a disk 16 on top of the IR window 14 by virtue of the surface 30 of piston 24. The piston 24 is put in by hand and pushed until its surface 32 abuts against surface 22 of the sample holder. At that time, the parts have been correctly dimensioned such that a predetermined space is left on the top of IR window 14 and that is the space to which the PTFE powder S is pressed to make the pressed disk 16.

As shown in FIG. 3, the pressed disc 16 is protected and tapped by an inserted wafer or disc 34 of plastic material which does not affect the optical characteristics of the standard. The wafer 34 is held in place by any suitable means, such as adhesive or by set screws.

As a preferred but non-limiting example, the sample holder may be fabricated from a rectangular block and will have a configuration to fit in and be held in an appropriate reflectance testing machine such as the TREBOR-70. The TREBOR-70 is an instrument that provides quantitative measurements of organic properties of any type of agro-foods by means of NIR reflectance and/or transmission measurements. (See Ser. No. 907,889. The sample holder is machined from a block of PVC approximately 3.30 inches long, 1.813 inches wide, and 1.26 inches high, which has appropriate indentions for attachment to the machine. The cavity is 1.563 inches in diameter plus 0.005, minus 0.000 and the thickness of the bottom lip and near-IR-quartz window is 0.063 inches. The cavity is filled with 12.4 grams of Halon, Dow Chemical's powdered PTFE. The piston has a smooth bottom surface and a slightly smaller diameter so it will slide smoothly into the standard holder, e.g. a diameter of 1.560 plus 0.000, minus 0.003. The distance from the face of the piston to the bottom of the flange is 0.500 inches, thus the piston fills about half of the cavity.

The pressed PTFE powder behind the near-IR-quartz window is used in the spectrum range above 8,800 angstroms up to approximately 30,000 angstroms and has been successfully incorporated into the TREBOR-70 unit. The advantages of using pressed PTFE as a reflectance standard are that such has from 96 percent to over 99 percent reflectivity through 2,600 nm; has effectively no absorptions in the wave lengths of interest; it is truly inert and does not optically change with time or temperature; it is totally non-hydroscopic and humidity does not affect its reflectivity value. In addition, when incorporated in the present invention, it is stable and can withstand normal handling without breaking despite otherwise fragility at the desired density.

I claim:

1. In combination with an analyzer for quantitative measurements for at least one constituent of interest in a sample by optical measurements, a calibration standard comprising, a calibration standared holder having a cup-shaped cavity closed at one end by an IR-quartz window, a pressed PTFE layer of a predetermined density and thickness in the cavity pressed onto and adjacent the IR-quartz window and having an upper surface substantially parallel to the surface against the IR-quartz window, and a sealing member in the cavity premanently sealing the pressed PTFE layer, the member being of a material which does not affect the optical characteristics of the standard.

2. A method of making a reflectance standard for use with optical measuring instruments, the standard being pressed powdered PTFE, the method comprising; placing a predetermined quantity of PTFE within a cavity and adjacent an IR-quartz window in the cavity, compressing the predetermined quantity of powdered PTFE with a piston in the cavity and positively limiting the movement of the piston to compress the powdered PTFE so as to produce the desired density powdered PTFE while also providing a relatively rugged non-fragile standard.

* * * * *

UNITED STATES PATENT AND TRADEMARK OFFICE
CERTIFICATE OF CORRECTION

PATENT NO. : 4,761,552

DATED : August 2, 1988

INVENTOR(S) : Robert D. Rosenthal

It is certified that error appears in the above-identified patent and that said Letters Patent is hereby corrected as shown below:

```
Column 2, line 62, after "907,889," add -- filed
     September 16, 1986). --;

Claim 1, line 4, delete "standared" and substitute
     therefor --standard--.
```

Signed and Sealed this

Thirteenth Day of June, 1989

*Attest:*

DONALD J. QUIGG

*Attesting Officer*   *Commissioner of Patents and Trademarks*